United States Patent [19]
Ribeiro et al.

[11] Patent Number: 5,763,271
[45] Date of Patent: Jun. 9, 1998

[54] VASODILATORY AND IMMUNE SUPPRESSANT PEPTIDES

[75] Inventors: Jose M. C. Ribeiro, Tucson, Ariz.; Richard G. Titus, Needham, Mass.; Charles B. Shoemaker, Weston, Mass.; Heinz G. Remold, Brookline, Mass.; Ethan A. Lerner, Newton, Mass.

[73] Assignee: The President and Fellows of Harvard College, Cambridge, Mass.

[21] Appl. No.: 233,597

[22] Filed: Apr. 26, 1994

Related U.S. Application Data

[63] Continuation-in-part of Ser. No. 137,691, Oct. 15, 1993, Pat. No. 5,397,772, which is a continuation of Ser. No. 778,159, filed as PCT/US90/03746, Jun. 29, 1990, abandoned, which is a continuation of Ser. No. 374,080, Jun. 29, 1989, abandoned.

[51] Int. Cl.$^6$ .................. C12N 1/21; C12N 5/10; C12N 15/12; C12N 15/63
[52] U.S. Cl. .................. 435/325; 435/252.3; 435/254.11; 435/320.1; 435/419; 536/23.5
[58] Field of Search .................. 536/23.5; 435/320.1, 435/240.2, 252.3, 325, 419

[56] References Cited

U.S. PATENT DOCUMENTS

| | | | |
|---|---|---|---|
| 4,839,343 | 6/1989 | Waeber et al. | 514/12 |
| 5,397,772 | 3/1995 | Ribeiro et al. | 514/12 |
| 5,480,864 | 1/1996 | Tajima et al. | 514/2 |

FOREIGN PATENT DOCUMENTS

| | | |
|---|---|---|
| 9100293 | 1/1991 | WIPO. |

OTHER PUBLICATIONS

Pabst et al. (1980), "Increased Production Of A Superoxide Anion By Macrophages Exposed In Vitro To Muramyl Dipeptide Or Lipopolysaccharide", *J. Exp. Med.*, vol. 151, pp. 101–114.
Amara et al. (1982), "Alternative RNA Processing In Calcitonin Gene Expression Generates mRNAs Encoding Different Polypeptide Products", *Nature*, vol. 298, pp. 240–244.
Johnson et al. (1983), "Sequential Activation Of Murine MononuclearPhagocytes For Tumor Cytolysis: Differential Expression Of Markers By Macrophages In The Several Stages Of Development", *J. Immunol.*, vol. 131(2), pp. 1038–1043.
Adams et al. (1984), "The Cell Biology Of Macrophage Activation", *Ann. Rev. Immunol.*, vol. 2, pp. 283–318.
Pickett et al. (1984), "Sequence Of An Antifreeze Protein Precursor", *Eur. J. Biochem.*, vol. 143, pp. 35–38.
Murray et al. (1985), "Activation Of Mouse Peritonal Macrophages In Vitro And In Vivo By Interferon", *J. Immunol.*, vol. 134(3), pp. 1619–1622.
Ribeiro et al. (1986), "Blood–Finding Strategy Of A Capillary–Feeding Sandfly, LKutzomyia Longipalpis", *Comp. Biochem. Physiol.*, vol.83A(4), pp. 683–686.
Buus et al. (1987), "The Interaction Between Protein–Derived Immunogenic Peptides And Ia", *Immunol. Reviews* vol., 98, pp. 115–141.
Unanue et al. (1987), "Membrane IL–1: A Key Protein In Antigen Presentation", *Ann. L'Institute Pasteur*, vol. 138, pp. 489–492.
Zaidi et al. (1987), "Biology Of Peptides From The Calcitonin Genes", *Quart. J. Experimental Physiol.*, vol. 72, pp. 371–408.
Titus et al. (1988), "Salivary Gland Lysates From The Sand Fly *Lutzomyia Longipalpis* Enhance Leishmania Infectivity", *Science*, vol. 239, pp. 1306–1308.
Tsunawaki et al. (1988), "Deactivation Of Macrophages By Transforming Growth Factor–B", *Nature*, vol. 334, pp. 260–262.
Umeda et al. (1988), "Inhibition Of Mitogen–Stimulated T Lymphocyte Proliferation By Calcitonin Gene–Related Peptide", *Biochem. Biophys. Research Conn.*, vol. 154(1), pp. 227–235.
Casini et al. (1989), "Effects Of Calcitonin Gene–Related Peptide (CGRP), Neurokinin A And Neurokinin A (4–10) On The Mitogenic Response Of Human Peripheral Blood Mononuclear Cells", *Naunyn–Schmiedeberg's Arch. Pharmacol.*, vol. 339, pp. 354–358.
Ribeiro et al. (1989), "A Novel Vasodilatory Peptide From The Salivary Glands Of The Sand Fly *Lutzomyia Longipalpis*", *Science*, vol. 243, pp. 212–214.
Brain et al. (1985), "Calcitonin gene–related peptide is a potent vasodilator", *Nature*, vol. 313, pp. 54–56.
Lerner et al. (1991), "Isolation Of Maxadilan, A Potent Vasodilatory Peptide From The Salivary Glands Of The Sand Fly *Lutzomyia Longipalpis*", *The Journal of Biol. Chem.*, vol. 266(17), pp. 11234–11236.
DaSilva et al. (1990), "Susceptibility Of Laboratory–Reared Female Lutzomyia Longipalpis (Lutz & Neiv, 1912) To Infection By Different Species And Strains Of *Leishmania Ross*, 1903", *Mem. Inst. Oswaldo Cruz*, vol. 85(4), pp. 453–458.
Lerner et al. (1992), "Maxadilan Cloning And Functional Expression Of The Gene Encoding This Potent Vasodilator Peptide", *The Journal of Biol. Chem.* vol., 267(2), pp. 1062–1066.
Theodos et al. (1993), "Salivary Gland Material From The Sand Fly *Lutzomyia Longipalpis* Has An Inhibitory Effect On Macrophage Function In Vitro", *Parasite Immunol.*, vol. 15, pp. 481–487.

(List continued on next page.)

*Primary Examiner*—Eric Grimes
*Attorney, Agent, or Firm*—Lahive & Cockfield, LLP; Jane E. Remillard; Amy E. Mandragouras

[57] ABSTRACT

Disclosed are proteins derived from the sand fly *Lutzomyia longipalpis* capable of inducing vasodilation in mammals and data characterizing the proteins and nucleic acids encoding the proteins. Also disclosed is a method for temporarily inactivating the immune system in a mammal comprising administering to the mammal the Lutzomyia protein, CGRP, calcitonin, or active immune suppressing analogs thereof.

25 Claims, 9 Drawing Sheets

OTHER PUBLICATIONS

Theodos, et al. (1991), "Analysis of Enhancing Effect Of Sand Fly Saliva On Leishmania Infection In Mice", *Infec. and Immun.*, vol. 59, pp. 1592–1598.

Samuelson et al. (1991), "A Mouse Model Of Leishmania Braziliensis Braziliensis Infection Produced By Coinjection With Sand Fly Saliva", *J. Exp. Med.*, vol. 173, pp. 49–54.

Nong et al. (1989), "Peptides Encoded By The Calcitonin Gene Inhibit Macrophage Function", *The Journal of Immunol.*, vol. 143, pp. 45–49.

Titus et al. (1990), "The Role Of Vector Saliva In Transmission Of Arthropod–Borne Disease", *Parastology Today*, vol. 6(5), pp. 157–160.

Nong et al. (1988), "Peptides Encoded By The Calcitonin Gene Inhibit Macrophage Function", *FASEB J.*, vol. 3, p. A479.

Theodos et al. (1990), "The Effect Of *Lutzomyia Longipalis* Salivary Gland Material On The Ability of Macrophages To Present Antigen To *Leishmania Major* Specific T Cells", *FASEB J.*, vol. 4, p. A2191.

Hall et al. (1993), "The Effect Of Sand Fly Saliva On Macrophage And T Cell Function In Leishmania Infection", *J. Immunol.*, vol. 150, p. 229A.

Ribeiro et al., Ann. Rev. Entomol. 32:463–478 (1987).

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..189

( x i ) SEQUENCE DESCRIPTION: SEQ ID NO:1:

```
TGT  GAT  GCA  ACA  TGC  CAA  TTT  CGC  AAG  GCC  ATA  GAT  GAC  TGC  CAG  AAG           48
Cys  Asp  Ala  Thr  Cys  Gln  Phe  Arg  Lys  Ala  Ile  Asp  Asp  Cys  Gln  Lys
 1                   5                        10                       15

CAG  GCG  CAT  CAT  AGC  AAT  GTT  TTG  CAG  ACT  TCT  GTA  CAA  ACA  ACT  GCA           96
Gln  Ala  His  His  Ser  Asn  Val  Leu  Gln  Thr  Ser  Val  Gln  Thr  Thr  Ala
                     20                       25                       30

ACA  TTC  ACA  TCA  ATG  GAT  ACC  TCC  CAA  CTA  CCT  GGA  AAT  AGT  GTC  TTC          144
Thr  Phe  Thr  Ser  Met  Asp  Thr  Ser  Gln  Leu  Pro  Gly  Asn  Ser  Val  Phe
           35                       40                       45

AAA  GAA  TGT  ATG  AAG  CAG  AAG  AAA  AAG  GAA  TTT  AAG  GCA  GGA  AAG               189
Lys  Glu  Cys  Met  Lys  Gln  Lys  Lys  Lys  Glu  Phe  Lys  Ala  Gly  Lys
      50                       55                       60

TAAAATGATT  GAAGAAAATT  GTAGCCGAGG  AGAGAAAGAA  AGAAAGTCCC  ATACCATATT                  249

TTGTTTGTTA  ATTGTAACGA  ATTTTCCGAA  AAATAAAAT   ATTATGCACT  CAATTTAAAA                  309

AAAAAA                                                                                  315
```

( 2 ) INFORMATION FOR SEQ ID NO:2:

( i ) SEQUENCE CHARACTERISTICS:
        ( A ) LENGTH: 63 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Cys  Asp  Ala  Thr  Cys  Gln  Phe  Arg  Lys  Ala  Ile  Asp  Asp  Cys  Gln  Lys
 1                   5                        10                       15

Gln  Ala  His  His  Ser  Asn  Val  Leu  Gln  Thr  Ser  Val  Gln  Thr  Thr  Ala
                     20                       25                       30

Thr  Phe  Thr  Ser  Met  Asp  Thr  Ser  Gln  Leu  Pro  Gly  Asn  Ser  Val  Phe
           35                       40                       45

Lys  Glu  Cys  Met  Lys  Gln  Lys  Lys  Lys  Glu  Phe  Lys  Ala  Gly  Lys
      50                       55                       60
```

( 2 ) INFORMATION FOR SEQ ID NO:3:

(i) SEQUENCE CHARACTERISTICS:
  (A) LENGTH: 243 base pairs
  (B) TYPE: nucleic acid
  (C) STRANDEDNESS: single
  (D) TOPOLOGY: linear (ii) MOLECULE TYPE: genomic DNA (ix) FEATURE:
  (A) NAME/KEY: CDS
  (B) LOCATION: 1..240

(xi) SEQUENCE DESCRIPTION: SEQ ID NO:3:

| ATG | AAA | TAT | TCT | TTA | AAT | AAT | CTC | CAT | TTT | CTT | GTA | GAC | GTT | GCT | GAG | 48 |
| Met | Lys | Tyr | Ser | Leu | Asn | Asn | Leu | His | Phe | Leu | Val | Asp | Val | Ala | Glu | |
| 1 | | | | 5 | | | | | 10 | | | | | 15 | | |

| GGC | TGT | GAT | GCA | ACA | TGT | CAA | TTT | CGC | AAG | GCC | ATA | GAA | GAC | TGC | AGG | 96 |
| Gly | Cys | Asp | Ala | Thr | Cys | Gln | Phe | Arg | Lys | Ala | Ile | Glu | Asp | Cys | Arg | |
| | | | 20 | | | | | 25 | | | | | 30 | | | |

| AAG | AAG | GCG | CAT | CAT | AGC | GAT | GTT | TTG | CAG | ACT | TCT | GTA | CAA | ACA | ACT | 144 |
| Lys | Lys | Ala | His | His | Ser | Asp | Val | Leu | Gln | Thr | Ser | Val | Gln | Thr | Thr | |
| | | 35 | | | | | 40 | | | | | 45 | | | | |

| GCA | ACA | TTT | ACA | TCA | ATG | GAT | ACC | TCC | CAA | CTA | CCT | GGA | AGT | GGT | GTT | 192 |
| Ala | Thr | Phe | Thr | Ser | Met | Asp | Thr | Ser | Gln | Leu | Pro | Gly | Ser | Gly | Val | |
| | 50 | | | | | 55 | | | | | 60 | | | | | |

| TTC | AAA | GAA | TGC | ATG | AAG | GAG | AAA | GCT | AAG | GAA | TTT | AAG | GCA | GGA | AAG | 240 |
| Phe | Lys | Glu | Cys | Met | Lys | Glu | Lys | Ala | Lys | Glu | Phe | Lys | Ala | Gly | Lys | |
| 65 | | | | | 70 | | | | | 75 | | | | | 80 | |

TAG 243

(2) INFORMATION FOR SEQ ID NO:4:

(i) SEQUENCE CHARACTERISTICS:
    (A) LENGTH: 80 amino acids
    (B) TYPE: amino acid
    (D) TOPOLOGY: linear (ii) MOLECULE TYPE: protein (xi) SEQUENCE DESCRIPTION: SEQ ID NO:4:

| Met | Lys | Tyr | Ser | Leu | Asn | Asn | Leu | His | Phe | Leu | Val | Asp | Val | Ala | Glu |
| 1 | | | | 5 | | | | | 10 | | | | | 15 | |

| Gly | Cys | Asp | Ala | Thr | Cys | Gln | Phe | Arg | Lys | Ala | Ile | Glu | Asp | Cys | Arg |
| | | | 20 | | | | | 25 | | | | | 30 | | |

| Lys | Lys | Ala | His | His | Ser | Asp | Val | Leu | Gln | Thr | Ser | Val | Gln | Thr | Thr |
| | | 35 | | | | | 40 | | | | | 45 | | | |

| Ala | Thr | Phe | Thr | Ser | Met | Asp | Thr | Ser | Gln | Leu | Pro | Gly | Ser | Gly | Val |
| | 50 | | | | | 55 | | | | | 60 | | | | |

| Phe | Lys | Glu | Cys | Met | Lys | Glu | Lys | Ala | Lys | Glu | Phe | Lys | Ala | Gly | Lys |
| 65 | | | | | 70 | | | | | 75 | | | | | 80 |

(2) INFORMATION FOR SEQ ID NO:5:

(i) SEQUENCE CHARACTERISTICS:
    (A) LENGTH: 384 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..258

(ix) FEATURE:
    (A) NAME/KEY: mat_peptide ( B ) LOCATION: 70..258

( x i ) SEQUENCE DESCRIPTION: SEQ ID NO:5:

```
ATG AAG CAA ATC CTT TTA ATC TCT TTG GTG GTG GTT CTT GCC GTG TTT        48
Met Lys Gln Ile Leu Leu Ile Ser Leu Val Val Val Leu Ala Val Phe
-23         -20             -15                     -10

GCC TTC AAC GTT GCT GAG GGC TGT GAT GCA ACA TGC CAA TTT CGC AAG        96
Ala Phe Asn Val Ala Glu Gly Cys Asp Ala Thr Cys Gln Phe Arg Lys
        -5              1               5

GCC ATA GAT GAC TGC CAG AAG CAG GCG CAT CAT AGC AAT GTT TTG CAG       144
Ala Ile Asp Asp Cys Gln Lys Gln Ala His His Ser Asn Val Leu Gln
10              15              20                      25

ACT TCT GTA CAA ACA ACT GCA ACA TTC ACA TCA ATG GAT ACC TCC CAA       192
Thr Ser Val Gln Thr Thr Ala Thr Phe Thr Ser Met Asp Thr Ser Gln
                30              35                      40

CTA CCT GGA AAT AGT GTC TTC AAA GAA TGT ATG AAG CAG AAG AAA AAG       240
Leu Pro Gly Asn Ser Val Phe Lys Glu Cys Met Lys Gln Lys Lys Lys
            45              50                      55

GAA TTT AGT TCA GGA AAG TAAAATGATT GAAGAAAATT GTAGCCGAGG              288
Glu Phe Ser Ser Gly Lys
        60

AGAGAAAGAA AGAAAGTCCC ATACCATATT TTGTTTGTTA ATTGTAACGA ATTTTCCGAA     348

AAAATAAAAT ATTATGCACT CAATTTAAAA AAAAAA                              384
```

( 2 ) INFORMATION FOR SEQ ID NO:6:

( i ) SEQUENCE CHARACTERISTICS:
( A ) LENGTH: 86 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Lys Gln Ile Leu Leu Ile Ser Leu Val Val Val Leu Ala Val Phe
-23         -20             -15                     -10

Ala Phe Asn Val Ala Glu Gly Cys Asp Ala Thr Cys Gln Phe Arg Lys
        -5              1               5

Ala Ile Asp Asp Cys Gln Lys Gln Ala His His Ser Asn Val Leu Gln
10              15              20                      25

Thr Ser Val Gln Thr Thr Ala Thr Phe Thr Ser Met Asp Thr Ser Gln
                30              35                      40

Leu Pro Gly Asn Ser Val Phe Lys Glu Cys Met Lys Gln Lys Lys Lys
            45              50                      55

Glu Phe Ser Ser Gly Lys
        60
```

( 2 ) INFORMATION FOR SEQ ID NO:7:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

GGGAATTCGC TAGCTGTGAT GCAACATG                                        28

( 2 ) INFORMATION FOR SEQ ID NO:8:

( i ) SEQUENCE CHARACTERISTICS:
   ( A ) LENGTH: 28 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:8:

```
GGGAAGCTTC CTCAATCTTT TACTTTCC                                              2 8
```

VASODILATORY AND IMMUNE SUPPRESSANT PEPTIDES

RELATED APPLICATIONS

This application is a continuation-in-part of U.S. Ser. No. 08/137,691, filed Oct. 15, 1993, now U.S. Pat. No. 5,397,772, issued Mar. 14, 1995, which is a continuation of U.S. Ser. No. 07/778,159, filed Jan. 5, 1992, now abandoned, which is a national phase United States application of PCT Application Number PCT/US90/03746, filed Jun. 29, 1990 and a continuation-in-part of U.S. Ser. No. 07/374,080, filed Jun. 29, 1989, now abandoned. The contents of these applications are hereby incorporated by reference.

GOVERNMENT FUNDING

The United States government may have rights to this invention pursuant to NIH grant numbers AI18694 and AI27511.

BACKGROUND OF THE INVENTION

Vasodilators are drugs useful in the treatment of various conditions characterized by constricted blood vessels. Such conditions include Raynaud's syndrome, certain post surgical complications of brain surgery involving sub arachnoid hemorrhage, heart failure, angina pectoris, and hypertension. Recently, the neuropeptide calcitonin gene-related peptide (CGRP) has been characterized as the most powerful and persistent vasodilator known. Calcitonin, another neuropeptide known primarily for its ability to prevent bone loss during periods of calcium stress, is derived from the same gene as CGRP. Despite weak structural homologies, there is enough similarity in the conformations of calcitonin and CGRP that they interact at each other's receptors. Thus, CGRP has a weak calcitonin-like effect on bone (Zaidi et al., Quart J. Exp. Physical, 72:371 (1987).

The macrophage, a large phagocytic cell of the reticuloendothelial system, plays a central role in the induction and expression of cellular immunity. Antigen processing and subsequent presentation of antigen by macrophages in the presence of class II histocompatibility antigens can trigger helper T-lymphocyte response (Buss et al., *Immunol. Rev.* 98: 115 (1987). In addition, macrophages can control T-cell responses via production of cytokines such as IL-1 (Unanue et al., *Ann. L'institute Pasteur* 138: 489 (1987)).

Activation of macrophages enhances the microbicidal and tumoricidal activity of the cells, an event which is paralleled by significant changes in the levels of various intracellular, secreted and cell surface proteins (Adams et al., *Ann. Rev. Immunol.* 2: 283 (1984)). For example, levels of secreted IL-1 and expressed class II histocompatability antigen rise, (Adams et al., ibid.) while the level of 5' nucleotidase has been shown to fall (Johnson et al., *J Immunol.* 131: 1038 (1983)). In addition, the production of $H_2O_2$ by activated macrophages is increased over controls (Adams et al., ibid.). Macrophages can be activated by a number of lymphokines such as IFN-γ (Merry et al., *J. Immunol.* 134: 1619 (1985)), and by bacterial cell wall products such as lipopolysaccharide (Pabst et al., *J. Exp. Med.* 151: 101 (1980)). Recently, it has been suggested that as activated macrophages sterilize the site of inflammation they are deactivated so as to avoid possible damage to host tissue via continued release of cytotoxic products. (Tsunawaki et al., *Nature* 334: 260 (1988)).

SUMMARY OF THE INVENTION

It has now been discovered that proteins derived from the salivary gland lysates of the sand fly *Lutzomyia longipalpis* are capable of inducing vasodilation and/or temporary immune suppression in mammals. These proteins are referred to herein as "Lutzomyia proteins" or "LP" proteins. In one embodiment, the LP protein is characterized by a molecular weight of about 6800 daltons, and as eluting prior to CGRP in an acetonitrile-$H_2O$-trifluoracetic acid-reverse phase-high performance liquid chromatography column. Its vasodilation activity is apparently at least 80 to 100 times as potent as CGRP, and like CGRP, persists for relatively long periods, e.g., several days.

Proteins derived from the salivary gland lysates of sand flies have been found to induce temporary immune suppression in a mammalian subject. Immune suppression is indicated by inhibition of macrophage function, e.g., prevention of increase of $H_2O_2$ production by γIFN or nitric oxide production and by suppression of the macrophage's ability to present antigen to T-cells.

The LP protein can be derived from lysate of the salivary glands of the sand fly by chromatographic purification as disclosed herein. Alternatively, the LP proteins of the invention and various active analogs and fragments thereof can be produced by expression of recombinant DNA in a host cell or by peptide synthesis techniques. The nucleotide sequence of a gene encoding an LP protein has been determined and the amino acid sequence deduced (SEQ ID NO:1 and 2). A second DNA sequence encoding another LP protein or LP variant has also been identified which varies somewhat from the first sequence determined both in terms of nucleotide sequence and the deduced amino acid sequence (SEQ ID NO:3 and 4). In addition to the LP variants described herein, another variant has been described by Lerner, E. A. and C. B. Shoemaker (1992) *J. Biol. Chem.* 267(2):1062–1066 and is shown in SEQ ID NO:5 and 6.

Compositions rich in one or more LP variants and fragments may be used pharmaceutically as an immunosuppressant agent or as a potent vasodilator. The active analogs and fragments of LP are typically proteins or peptides comprising an amino acid sequence sufficiently duplicative of the sequence of the active portion of an LP protein such that the proteins or peptides are capable of inducing vasodilation or temporary immune suppression in a mammal.

Thus, in another aspect, the invention comprises a method of increasing blood flow in the circulatory system of a mammal by administering to the mammal an effective amount of LP, or active analog or fragment thereof, to cause vasodilation in the mammal. Parenteral administration can result in systemic vasodilation activity. Topical application, e.g., to a vascular bed during surgery, can serve to concentrate the vasodilatory effect in the locus of application.

In another aspect, it has been discovered that, in addition to LP, the structurally related CGRP and calcitonin peptides also can be used to suppress the immune system temporarily. The invention thus further provides a method of desensitizing a mammal to the effects of an immunogen by parenterally administering LP, calcitonin, CGRP, active analogs or fragments thereof, or mixtures thereof in amounts effective to temporarily inactivate the immune system. Thus, for example, these temporary immune suppressing substances may be administered in conjunction with a protein xenotypic to the mammal (such as streptokinase or a murine monoclonal in man) so as to inhibit or prevent the development of antibodies or cellular immunity to the drug. The immune suppressing substances may also be used to treat graft rejection and autoimmune disease.

DETAILED DESCRIPTION OF THE INVENTION

Figure 1:
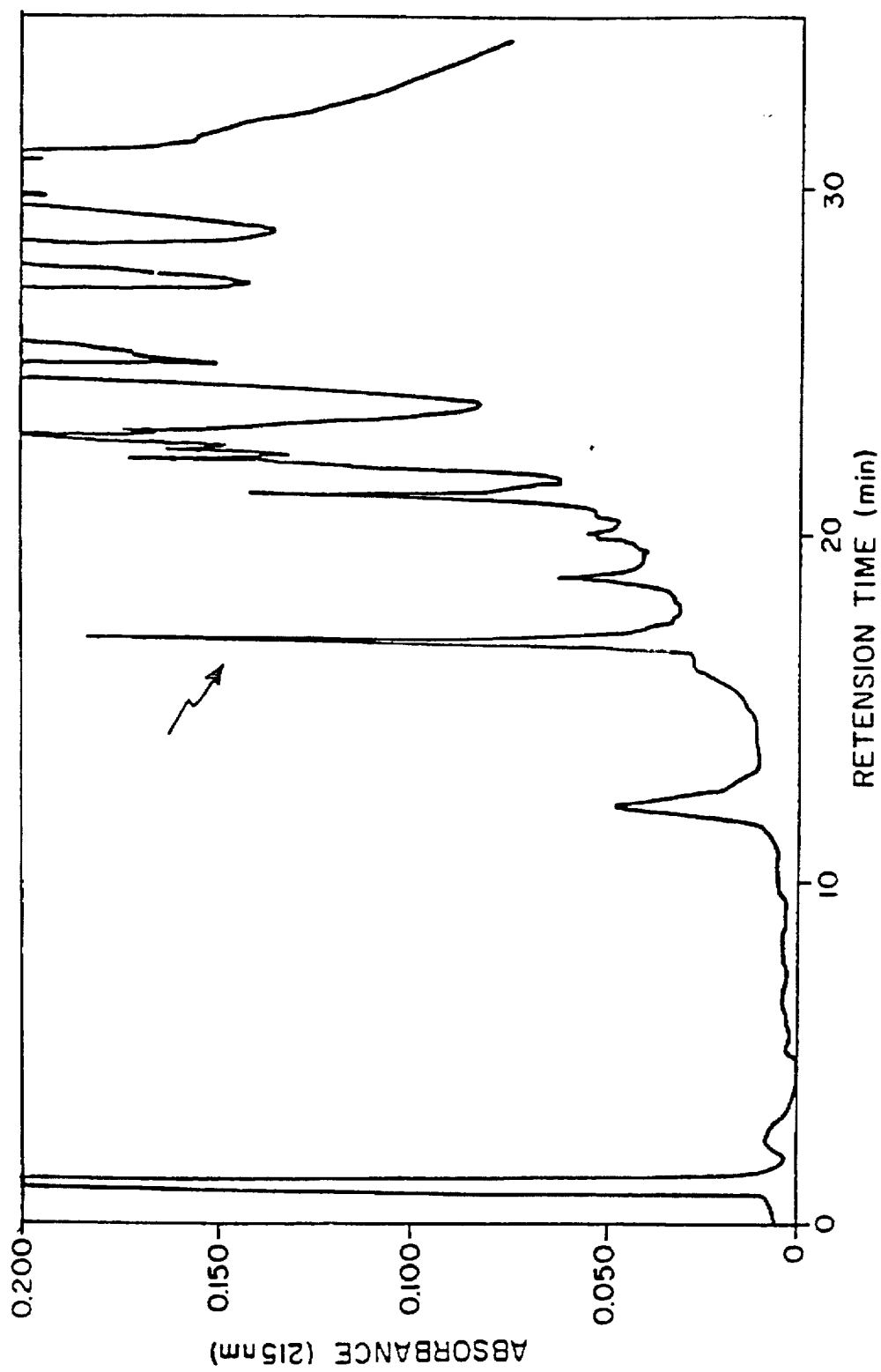
FIG. 1 shows a reverse-phase HPLC chromatogram of salivary gland extract.
Figure 2:
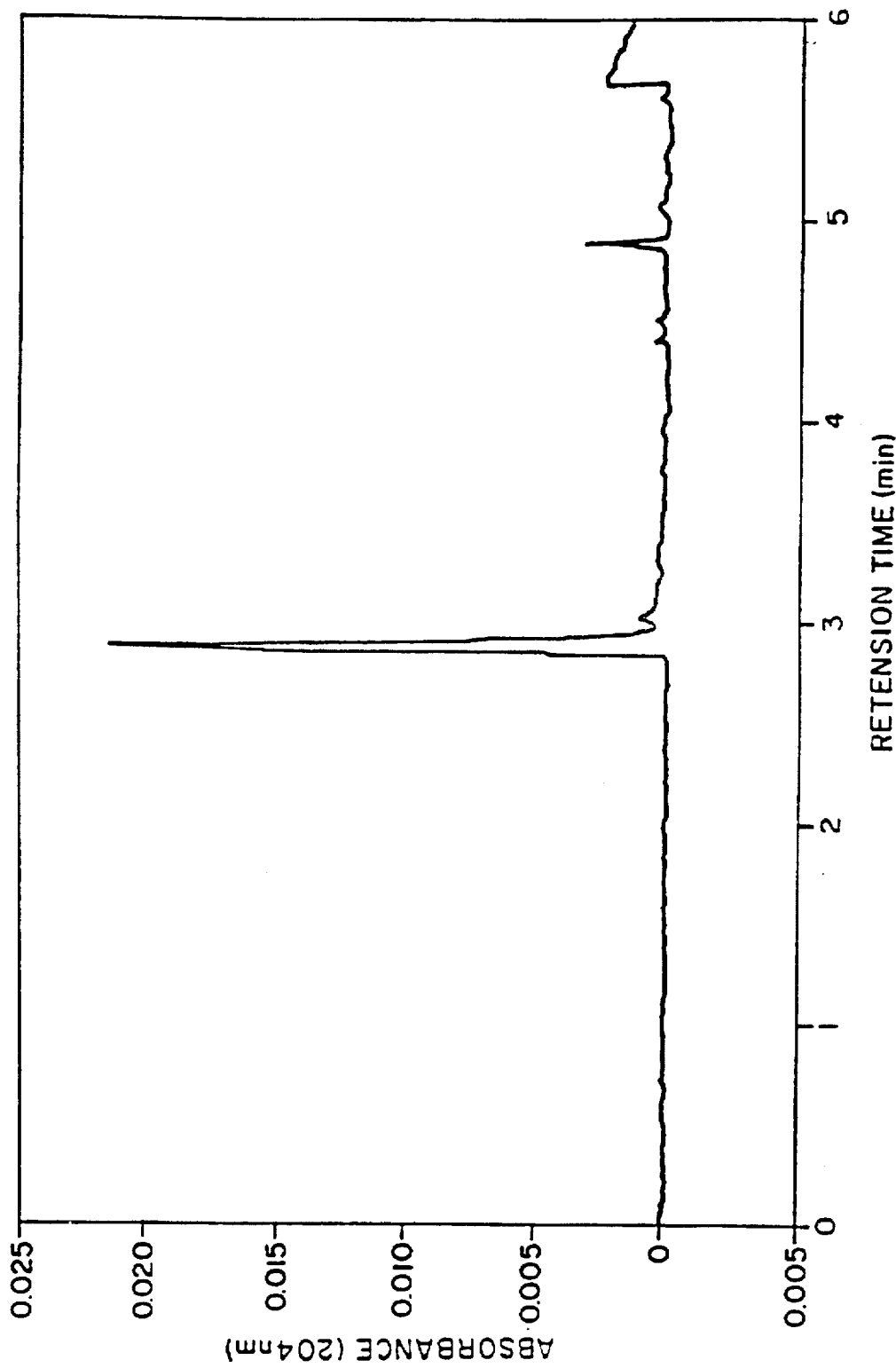
FIG. 2 shows the results of capillary electrophoresis of reverse-phase HPLC purified LP.
Figure 3:
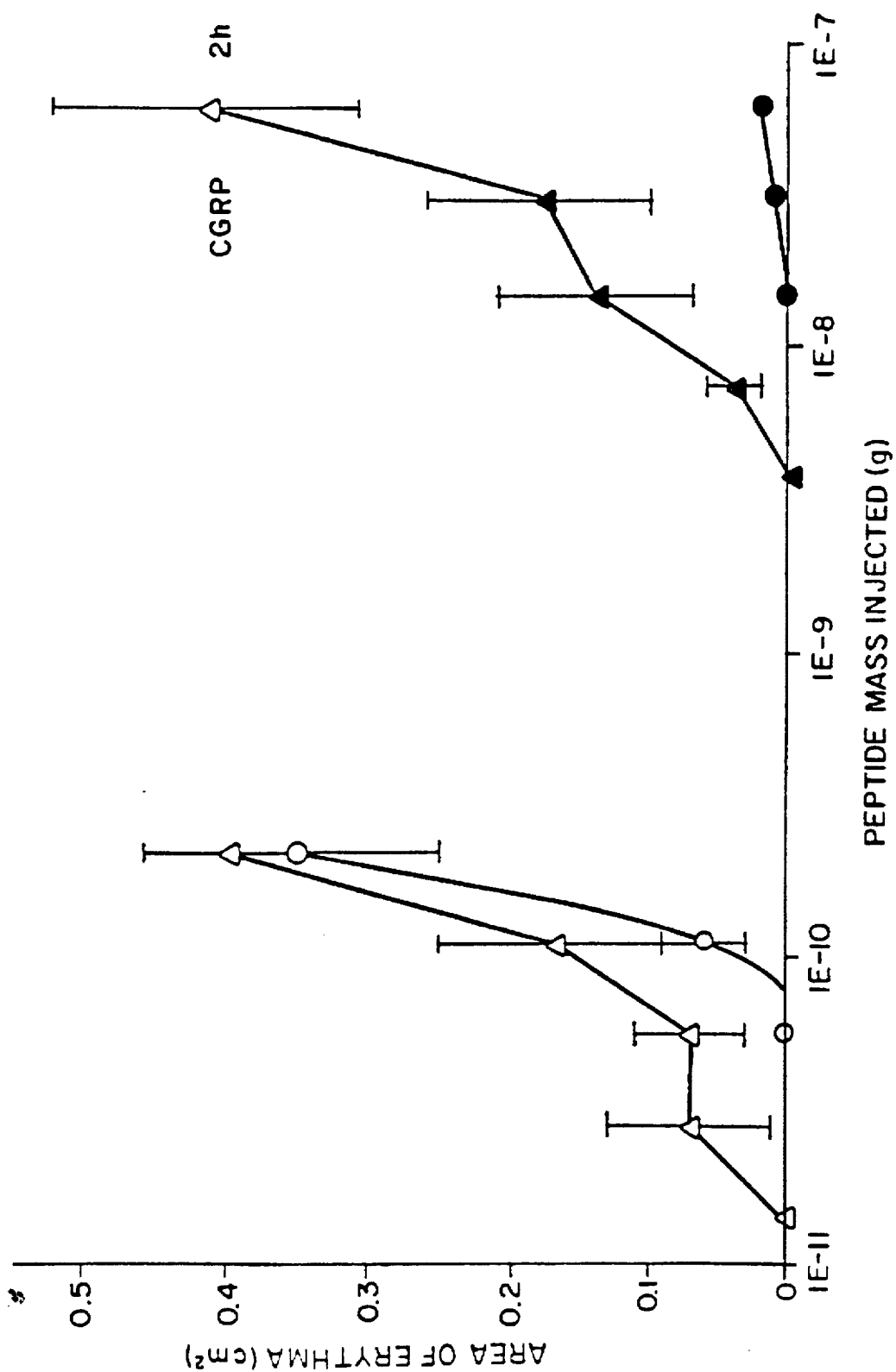
FIG. 3 is a graph showing the potency and persistence of erythema induced by LP and CGRP.

Active proteins derived from the salivary gland lysates of the sand fly *Lutzomyia longipalpis* have been identified and shown to have vasodilatory and/or immunosuppressive activity. In addition, it has been discovered that calcitonin, CGRP and LP proteins all exhibit an ability to suppress temporarily the immune system of mammals.

Isolated proteins within the scope of the invention are exemplified by the "Lutzomyia proteins" or "LP" proteins shown in the sequence listing (i.e., SEQ ID NO:1, 2, 3, 4, 5 and 6). Proteins suitable for use in the methods and compositions of the present invention include those proteins extracted and purified from the lysate of salivary glands of sand fly, active analogs and active fragments thereof, or recombinantly produced peptides. For example, an LP protein can be obtained by conventional purification chromatography from surgically excised salivary glands of *L. longipalpis* as disclosed below.

Isolated nucleic acids encoding an LP protein can be obtained from MRNA present in salivary glands of *Lutzomyia longipalpis*. It should also be possible to obtain nucleic acids encoding an LP protein from *Lutzomyia longipalpis* genomic DNA. For example, the gene encoding an LP protein can be cloned from either a cDNA or genomic library, as described in the examples below. A cDNA encoding an LP protein can be obtained by isolating total mRNA from *Lutzomyia longipalpis* sand flies. Double stranded cDNAs can then be prepared from the total MRNA. Subsequently, the cDNAs can be inserted into a suitable plasmid or bacteriophage vector using any one of a number of known techniques as described above. Genes encoding an LP protein can also be cloned using established polymerase chain reaction techniques in accordance with the nucleotide sequence information provided by the invention.

Accordingly, one aspect of the invention provides an isolated nucleic acid encoding an LP protein which comprises a nucleotide sequence shown in SEQ ID NO:1 or SEQ ID NO:3, or a fragment thereof which encodes an LP peptide having vasodilatory or immunosuppressive activity. The nucleic acid shown in SEQ ID NO:3 comprises a 51 base leader sequence followed by a coding region corresponding to bases 52 through 240. This nucleic acid encodes a mature protein comprising amino acid residues 18–80 of SEQ ID NO:4.

As used herein, the term "isolated Lutzomyia protein" or "isolated LP protein" refers to peptides, active analogs, and active fragments. The term "isolated" refers to a protein, peptide or nucleic acid which is substantially free of nucleic acids, proteins and peptides with which the nucleic acid, protein or peptide naturally occurs (i.e., other sand fly proteins and peptides) either in a cell or when secreted by a cell, or substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived.

Knowledge of the nucleotide and amino acid sequences of the LP proteins of the invention enables skilled engineers to produce large quantities of the protein for therapeutic use. The artisan can synthesize an LP protein or active analogs thereof using conventional chemical solid or solution phase peptide synthesis techniques. In addition, knowledge of the sequence permits expression of DNA sequence coding for an LP protein or active analogs or fragments thereof in various types of host cells, including both procaryotes and eucaryotes, to produce large quantities of the protein, or active analogs or fragments thereof, and other constructs capable of inducing vasodilation or temporary immune suppression in a mammal. Thus, a gene encoding the amino acid sequence, or various analogs thereof, can be produced, for example, by oligonucleotide synthesis and subsequent ligation if necessary to form a complete coding region. The coding region may be ligated to 3' and 5' untranslated DNA regions constituting, as required, a poly A site, promoter, ribosome binding site, stop and start codons, etc. Fused DNAs, e.g., comprising DNA coding for a host polypeptide and LP polypeptide can be used for production of fusion proteins comprising LP polypeptides. The construction of an expression vector suitable for production of LP products in a selected cell type also is within the skill of the art. Culture of transformed cells results in intracellular accumulation or secretion of protein which may be purified, refolded, and otherwise post translationally modified as desired or as necessary.

To produce LP proteins or fragments thereof having vasodilatory or immunosuppressive activity by recombinant DNA techniques, an expression vector containing a nucleic acid encoding all or a portion of an LP protein (e.g., SEQ ID NO:1, 3, 5), operably linked to at least one regulatory sequence can be used. Operably linked is intended to mean that the nucleotide sequence is linked to a regulatory sequence in a manner which allows expression of the nucleotide sequence. Regulatory sequences are art-recognized and include promoters, enhancers and other expression control elements. Such regulatory sequences are described in Goeddel, Gene Expression Technology: Methods in Enzymology 185, Academic Press, San Diego, Calif. (1990). It should be understood that the design of the expression vector may depend on such factors as the choice of the host cell to be transformed and/or the type of protein desired to expressed. In one embodiment of the present invention, the expression vector includes nucleic acid, preferably a DNA, encoding an LP protein or fragment having immunosuppressive activity, such as a protein having all or a portion of the amino acid sequence shown in SEQ ID NO:4. Such expression vectors can be used to transfect cells to thereby produce proteins or peptides, including fusion proteins or peptides encoded by nucleic acids as described herein.

Host cells suitable for transfection and recombinant production of LP proteins include any procaryotic or eucaryotic cell. For example, an LP protein or peptide may be expressed in bacterial cells such as *E. coli*, insect cells (baculovirus), yeast, or mammalian cells such as Chinese hamster ovary cells (CHO). Other suitable host cells can be found in Goeddel, (1990) supra or known to those skilled in the art.

Isolated LP protein or fragments thereof having vasodilatory or immunosuppressive activity can also be chemically synthesized, using techniques known in the art such as conventional Merrifield solid phase f-Moc or t-Boc chemistry. The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (see e.g., Itakura et al, U.S. Pat. No. 4,598,049; Caruthers et al., U.S. Pat. No. 4,458,066; and Itakura, U.S. Pat. Nos. 4,401,796 and 4,373,071, incorporated by reference herein).

Isolated nucleic acids which encode an LP protein or a fragment thereof having vasodilatory or immunosuppressive activity, and which have a sequence which differs from the nucleotide sequence shown in SEQ ID NO:1, 3 or 5 are also within the scope of the invention. Such nucleic acids encode functionally equivalent LP proteins having vaosdilatory or immunosuppressive activity but differ in sequence from the sequence shown in SEQ ID NO:1, 3 or 5 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of an LP protein. However, it is expected that DNA sequence polymorphisms that do lead to changes in the amino acid sequence of an LP protein will exist within the sand fly population. One skilled in the art will appreciate that these variations in one or more nucleotides (up to about 3-4% of the nucleotides) of the nucleic acids encoding LP proteins and peptides may exist among sand fly populations due to natural allelic variation. Any and all such nucleotide variations and resulting amino acid polymorphisms are within the scope of this invention.

Fragments of the nucleic acid encoding an LP protein of the invention which encode peptides having vasodilatory or immunosuppressive activity are also within the scope of the invention. As used herein, a fragment of the nucleic acid encoding an LP protein refers to a nucleotide sequence having fewer nucleotides than the nucleotide sequence encoding the entire amino acid sequence of an LP protein and which encodes a peptide having vasodilatory or immunosuppressive activity.

Preferred nucleic acid fragments encode peptides of at least about 10 amino acid residues in length, preferably about 10-20 amino acid residues in length, and more preferably about 12-16 amino acid residues in length. Nucleic acid fragments of an LP protein having vasodilatory or immunosuppressive activity and which are at least about 30 amino acid residues in length, at least about 40 amino acid residues in length and at least about 60 amino acid residues in length or more are also within the scope of this invention.

Generally, nucleic acids encoding an LP protein having vasodilatory or immunosuppressive activity will be selected from the bases encoding the mature LP protein. However, in some instances it may be desirable to select all or part of a peptide from the leader sequence portion of the nucleic acids of the invention. Nucleic acids within the scope of the invention may also contain linker sequences, modified restriction endonuclease sites and other sequences useful for molecular cloning, expression or purification of recombinant an LP protein or fragments thereof.

Fragments of the nucleic acid encoding an LP protein which encode peptides having vasodilatory or immunosuppressive activity can be obtained, for example, by screening peptides recombinantly or synthetically produced from portions of the nucleic acid or amino acid sequences shown in SEQ ID NO:1, 2, 3 and 4. Tests to identify vasodilatory or immunosuppressive activity of a protein or peptide are described herein in detail in the Exemplification section. For example, assays for identifying proteins or pepides having immunosuppressive activity include those which measure reduced macrophage activity as indicated by, for example, a decrease in $H_2O_2$ production or nitric oxide production by macrophages.

Isolated LP protein and fragments thereof having vasodilatory or immunosuppressive activity can be administered to subjects in the form of pharmaceutical compositions for therapeutic use. Thus, the invention provides compositions suitable for pharmaceutical administration comprising an isolated LP protein or fragment thereof having vasodilatory or immunosuppressive activity and a pharmaceutically acceptable carrier. In particular, LP proteins can find use as a therapeutic vasodilating agent and consequently as a regulator of blood pressure. Also, CGRP and calcitonin (both available commercially) as well as LP may be used to induce temporary immune suppression. As a therapeutic vasodilating agent, these compounds can be administered to mammalian hosts for veterinary use such as with domestic animals, and for clinical use in humans in a manner similar to other therapeutic agents. In general, the dosage will range from about 2 pg to 0.25 µg per kg of host body weight. Dosages within 5 these ranges can be used in an amount per administration which may vary depending on the severity of the condition treated until benefits have been obtained. The protein can be injected intravascularly to provide a systemic vasodilation effect to treat, for example, Raynaud's syndrome. It also may be applied topically or by infusion to induce locally a vasodilatory action, for example, during brain surgery to alleviate blood vessel constriction and subsequent brain damage. These compounds may be formulated for oral, buccal, parenteral, or rectal administration or in a form suitable for nasal administration or administration by inhalation or insufflation.

Alternatively, LP proteins or fragments thereof having immunosuppressive activity can be administered to a subject to induce temporary immune suppression in the subject to a therapeutic immunogen. Administration of compositions including an LP protein or active fragment can be carried out using known procedures, at dosages and for periods of time effective to prevent or suppress an immune response in a subject to an immunogen. The term subject is intended to include living organisms in which an immune response can be elicited, e.g., mammals. Examples of subjects include humans, dogs, cats, mice, rats and transgenic species thereof. An amount of an LP protein or fragment thereof necessary to achieve a therapeutic effect may vary according to factors such as the degree of sensitivity of the subject to dog dander, the age, sex, and weight of the subject. Dosage regima may be adjusted to provide the optimum therapeutic response. For example, several divided doses may be administered daily or the dose may be proportionally reduced as indicated by the exigencies of the therapeutic situation.

Accordingly, an isolated LP protein of the invention, and fragments thereof having immunosuppressive activity, can be used therapeutically to modify or suppress immune responses in a subject, such as a mammal, to a variety of immunogens. For example, LP proteins and peptides of the invention can be administered to a subject in conjunction with antibodies, blood cells, bone marrow, tissues or organs which are allogeneic or xenogeneic to the subject in order to prevent or reduce rejection of the foreign proteins. The proteins and peptides of the present invention can also be administered to a subject in conjunction with a drug to prevent or reduce an allergic reaction in the subject to the drug.

Thus, this invention provides methods for inducing immunosuppression to an allogeneic or xenogeneic cell in a transplant recipient comprising administering to the recipient an isolated LP protein or fragment thereof having immunosuppressive activity and an allogeneic or xenogeneic cell. Such methods are particularly useful for inducing immune suppression in a bone marrow or tissue or organ transplant recipient. As used herein, the term "recipient" refers to a subject into whom a tissue or organ graft or bone marrow is to be transplanted, is being transplanted or has been transplanted. As defined herein, the term "allogeneic" means obtained from a different individual of the same species as the recipient. Allogeneic tissue, organ or bone marrow cells express "alloantigens", which differ from antigens expressed by cells of the recipient. As defined herein, the term "xenogeneic" means obtained from a different species than the recipient. Xenogeneic tissue, organ or bone marrow cells express "xenoantigens", which differ from antigens expressed by cells of the recipient. As used herein, the term "donor antigens" means antigens expressed by the donor tissue, organ or bone marrow cells to be transplanted into the recipient. The donor antigens may be alloantigens or xenoantigens, depending upon the source of the graft. The allogeneic or xenogeneic tissue, organ or bone marrow cells are preferably obtained from the donor of the tissue, organ or bone marrow but can be obtained from one or more sources having common antigenic determinants with the donor.

The isolated LP proteins of the invention or fragment thereof can be used for the production of antibodies directed against the protein or a portion thereof, such as anti-LP protein monoclonal antibodies. Such antibodies are useful for the detection and purification of an LP protein in a biological sample.

In the form of a pharmaceutical composition, an LP protein of the invention or fragments thereof may be administered in a convenient manner such as by injection (subcutaneous, intravenous, etc.), oral administration, inhalation, transdermal application, or rectal administration. Depending on the route of the administration, the active compound (e.g., LP protein) may be coated in a material to protect the compound from the action of enzymes, acids and other natural conditions which may inactivate the compound.

To administer an LP protein or peptide by other than parenteral administration, it may be necessary to coat the protein or peptide with, or co-administer the protein or peptide with, a material to prevent its inactivation. For example, an LP protein may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil water CGF emulsions as well as conventional liposomes (Strejan et al. (1984) *J. Neuroimmunol.*, 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound such as an LP protein or fragment thereof having vasodilatory or immunosuppressive activity in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile filtered solution thereof.

When an LP protein or peptide is suitably protected, as described above, the protein or peptide may be orally administered, for example, with an inert diluent or an assimilable edible carrier. The protein or peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 5 to about 80% of the weight of the unit. The amount of active compound in such therapeutically useful compositions is such that a suitable dosage will be obtained.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in subjects.

The invention is further illustrated by the following example which should not be construed as limiting. The contents of all references, patents and published patent applications cited throughout this application are hereby incorporated by reference.

EXAMPLE 1

Isolation of LP Proteins From *Lutzomyia longipalpis*

Sand flies were reared from a laboratory strain of *Lutzomyia longipalpis* originally provided by the Walter Reed Army Institute of Research following the procedure described by Modi et al., *J. Med. Entomol.* 20: 568–570 (1983). Wild specimens can be captured in various tropical regions in South America. Larvae were fed a mixture of fermented rabbit feed (Purina), rabbit faeces, and liver powder. Adults were kept at 100% relative humidity and were given free access to a saturated sucrose solution. Salivary glands are dissected from 5–7 day old female flies and stored in phosphate-buffered saline containing 1 mg/ml bovine serum albumin (PBS-BSA). The glands are excised using a #5 forceps and surgical needles to remove the prominent glands posterior to the head. Pairs of glands are transferred to 20 μl of Tris-HCl buffer, 5 mM, pH 7.4, and may be frozen at −70° C. until needed.

EXAMPLE 2

Characterization of an LP Protein

Reversed-phase high-performance liquid chromatography (HPLC) on the extract of 100 pairs of salivary glands is depicted in FIG. 1. 100 pairs of salivary glands were dissected in PBS. Lysates were made by freeze-thawing. The extract was spun in a microcentrifuge for 30 seconds before being applied to the column. A C-18 micropellicular HPLC column (Glycotech) was equilibrated with 20% acetonitrile/0.1% trifluoroacetic acid at 50° C. at a flow rate of 0.6 ml/minute. Three minutes after injection, a linear gradient was run for 20 minutes reaching 44% acetonitrile. Fractions were collected every 30 seconds and assayed for vasodilatory activity. The vasodilator assay was performed by diluting material from the gradient 10 fold and injecting 50 μl intradermally into the shaved back of a rabbit. The development of erythema at the injection site corresponded with the peak indicated. One μg of human CGRP, used as a control peptide, eluted as a peak of equal area, five minutes later. This observation implies that approximately 10 nanograms of LP are present per pair of salivary glands.

Because multiple components could be hidden under a single peak from HPLC, an independent measure of LP purity was needed. Capillary electrophoresis, which can separate molecules on the basis of charge, was chosen. The limitation here was the need to have a volume of a few microliters where the concentration of LP would approximate the 1 mg/ml used in capillary electrophoresis. 250 pairs of salivary glands were dissected and 2.5 μg of LP isolated from multiple runs on RP-HPLC. The fractions containing LP were pooled, yielding a volume of approximately 2 ml. LP was concentrated in a Speed-Vac to a volume of 10 μl in preparation for capillary electrophoresis. Sample was injected for three seconds at ½ psi and electrophoresed at 25 kv on a Beckman P/ACE 2000 instrument. A 100 mM borate buffer of pH 8.3 was chosen because isoelectic focusing of the HPLC-purified EIP revealed activity at a pI of 7.8. The sloping peak near six minutes represents trifluoroacetic acid remaining from the HPLC run. A large peak was present after nearly three minutes of electrophoresis (FIG. 2). 0.5 microgram of RP-HPLC purified LP was analyzed via fast-atom-bombardment (FAB) mass spectrometry in order to determine its mass. A single component of 6839 mass units was detected. The mass of LP is thus different from that of 3900 for CGRP.

The vasodilatory activity of RP-HPLC purified LP as compared to synthetic human α-CGRP on rabbit skin is shown in FIG. 3. The amount of LP injected into the skin was based on the area of the absorbing peak collected from RP-HPLC. The indicated amounts of RP-purified LP or synthetic CGRP, in a volume of 50 μl of PBS, were injected into the shaved back of a rabbit. The area of resultant erythema was measured at 2 hours (triangles) and again at 4 hours (circles). Bars represent average and SE of triplicate injections. Two hours after injection, 0.1 nanograms of LP gives an erythema equivalent to 50 nanograms of CGRP. At 4 hours, erythema from LP is still present whereas the CGRP injection site has only residual erythema.

EXAMPLE 3

Demonstration of Vasodilatory Activity of an LP Protein

The vasodilatory activity of the LP is shown by the relaxation of a constricted rabbit aortic ring by *Lutzomyia longipalpis* salivary glandlysates. In FIG. 4, A indicates the addition of adrenaline, 200 mg total; S represents the addition of the salivary gland lysate from three sand flies (approx. 30–40 ng LP); and W represents the washing of the preparation. Thoracic aortas were obtained from adult New Zealand rabbits. 4 mm-wide rings were suspended on a 3-ml bath containing Tyrode's solution bubbled with 95% $O_2$ and 5% $CO_2$ and kept at 37° C. under initial tension of 1 g (Webster et al., *Meth. Enzymol.* 293: 531 (1970)).

Figure 4:
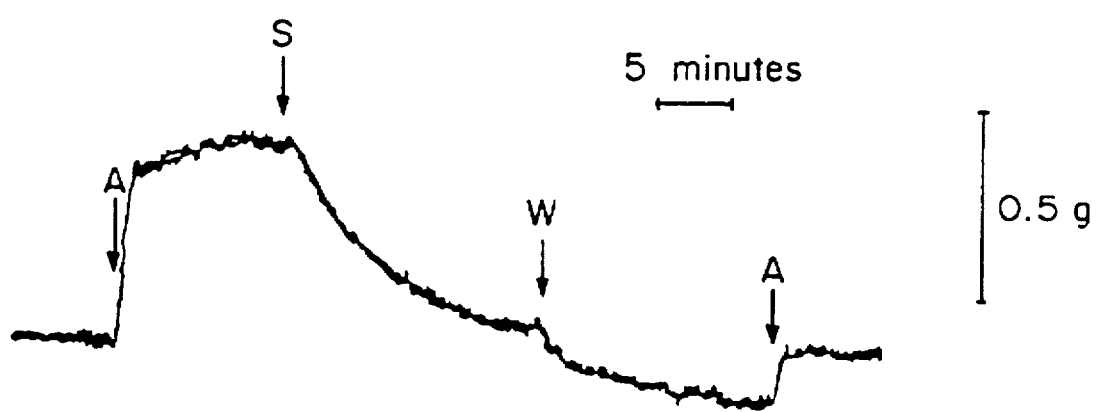
FIG. 4 is a graph representing the level of relaxation of a constricted rabbit aortic ring by *Lutzomyia longipalpis* salivary gland lysate measuring tension vs. time; A indicates addition of the vasoconstrictor adrenalin; S indicates addition of salivary gland lysates; W represents washing of the preparation; the second A represents a second addition of adrenalin.

An auxotonic pendulum level (Paton, *J. Physiol. Lond.* 137: 35P–36P (1957) coupled to a Harvard isotonic transducer served to measure the contractions. In four experiments, relaxation of more than 50% was achieved when homogenate from 3 pairs of glands were added to the 2.5 ml chamber (58±8%, mean±S.E.). In all cases there was a 15–30 second delay between addition of the salivary homogenate and beginning of the relaxation. After the preparation was washed, further addition of adrenaline did not restore the pre-treatment level of contraction, indicating that the activity persisted (FIG. 4). The duration of the erythema induced by LP upon injection into mammalian skin suggests the vasodilation activity lasts at least 24 hours.

EXAMPLE 4

Amino Acid Sequence Determination of an LP Protein

HPLC-purified biologically active LP was subjected to amino acid micro-sequencing. Amino acid residues 3–13 were determined but not residues 1 or 2 of the mature protein sequence. A degenerate oligonucleotide was used in conjunction with an oligo-dT primer in the polymerase chain reaction to directly amplify a minuscule amount of LP cDNA which had been made from about 60 cells, or ⅕th of a pair of salivary glands. This amplified DNA sequence was missing the most 5' end coding for amino acids 1 and 2 and upstream sequences including the signal sequence and promoter. However, this DNA sequence yielded the nucleotide sequence 3' to the nucleotides coding for amino acid residue 14. This sequence information was used to select a genomic clone from a sand fly genomic library. A new oligonucleotide was then prepared from the genomic DNA which had the sequence from the signal peptide, along with an oligonucleotide from the 3' untranslated region of the LP cDNA.

These oligonucleotides were used as primers to amplify the cDNA coding for the complete sequence, including residues 1 and 2, which was then sequenced by standard technique. The nucleotide sequence of the cDNA and the deduced amino acid sequence of the mature LP is shown as SEQ ID NO:1. The genomic LP DNA sequence, shown as SEQ ID NO:3, varies somewhat from the LP cDNA sequence and is believed to represent a variant LP gene and includes the DNA sequence and deduced amino acid sequence of the 17 amino acid leader peptide (SEQ ID NO:4). The signal sequence of LP is also given in sequence 2 (nucleotides 1–51, SEQ ID NO:3).

EXAMPLE 5

Solid Phase Peptide Synthesis of LP Proteins

The LP peptide may be prepared conveniently using standard solid-phase peptide synthesis (Merrifield, *Fed Proc. Fed. Amer. Soc. Exp. Biol.* 24:412 (1962)). In such a synthesis, the solid phase support acts as a C-terminal protecting group for the growing oligomer chain. Thus, in general, N-terminal protected amino acid or peptide is reacted with a suitably functionalized and soluble polymer such that the C-terminal residue is attached to the insoluble support. The N-terminal protecting group is then selectively removed from the aminoacyl polymer and the next N-protected amino acid or peptide is coupled to the polymer using a suitable reagent for reaction of the carboxyl group of the amino acid or peptide to be introduced. The cycle of deprotection and coupling can be repeated as necessary, using the appropriate amino acid or peptide derivatives, to assemble on the polymer carrier the desired amino acid sequence of the peptide. Once the sequence is complete, a more rigorous reagent is applied to the peptide/polymer, to cleave the bond linking the peptide to the polymer, thus liberating the peptide which can be recovered using conventional techniques. Depending on the conditions used, the peptide may have a C-terminal acid or amide group and may, or may not, possess a N-terminal protecting group.

It will also be appreciated that any other reactive group(s) such as amino, carboxy, hydroxy, or mercapto group(s) if present, will have been suitably protected during the synthesis and may still be in a protected state after cleavage of the peptide from the polymer. Further processing of the peptide is therefore often necessary to obtain the desired compound.

Peptide synthesis including the introduction and removal of protective groups is well known in the art. See for example "The Peptides" Volume 3, Gross and Meienhoffer, Academic Press, 1981. The amino acid or peptide starting materials, or reactive derivatives thereof for use in the solid phase synthesis, are either known compounds, or may be prepared by methods analogous to those used for the preparation of the known compounds. Particular reagents which may be used for activation of the carboxyl group of the amino acid or peptide include for example imides such as dicyclohexylcarbodiimide.

The resin may be, for example, an insoluble polymeric support, e.g. a polyamide resin such as a cross-linked polydimethylacrylamide resin or any inert macroreticular resin such as polystyrene 5 cross-linked with divinyl benzene or a methyl benzhydrylamine resin.

Two procedures have been found which are useful in the preparation of compounds of the invention. The first of these is the BOC procedure, where the protectant group used in the synthetic cycle is a tertiary butoxycarbonyl group. The BOC protectant group is selectively removed at each stage using trifluoroacetic acid and dichloromethane. After completion of the synthetic cycles the peptide is removed from the resin by treatment with hydrogen fluoride and anisole. The second procedure is known as the FMOC procedure and utilizes a fluorenylmethoxycarbonyl group which is selectively removed using 20% piperidine in dimethylformamide. The peptide is cleaved from the resin by treatment with trifluoroacetic acid and anisole.

Calcitonin and CGRP have a C-terminal amide group which is necessary for activity. If LP requires amidation, it may be provided by appropriate choice of the cleavage conditions used in the solid phase synthesis described above. Thus, the compound may be cleaved from the support and amidated in a one-step process by treatment with, for example, methanol and ammonia. Alternatively, where the cleavage conditions are chosen to yield a peptide with a C-terminal carboxylic acid, the amide, if necessary, may be obtained by conventional means, for example where the penultimate C-terminal residue is leucine, by enzymatic treatment with carboxypeptidase Y, and where the penultimate residue is glycine, with amidating enzyme (Bradbury, et. al., *Nature* 298:240–244 (1982)), or by chemical treatment of the peptide with, for example, ammonia. Alternatively solution phase peptide synthesis techniques may be used for preparation of the LP peptide.

EXAMPLE 6

Temporary Immune Suppression

A. Assay of $H_2O_2$ Production by Macrophages as a Marker of Immune Stimulation Monocytes obtained by leukophoresis of healthy volunteers were purified on Ficoll-hypaque and Percoll (Pharmacia, Piscataway, N.J.) gradients and placed into microtiter well ($5\times10^5$/well) in RPMI-1640 (GIBCO, Grand Island, N.Y.) with 5% pooled normal human serum and 1% gentamycin (M. A. Bioproducts, Walkinville, Md.). The cells were greater than 95% macrophages as judged by esterase staining. (*The Manual of Macrophage Methodology*, Herrscowitz et al., eds. Marcel Dekker, N.Y., p. 199 (1981)). After one day in culture, non-adherent cells were rinsed away and the macrophages were treated, e.g., with human CGRP, Calcitonin, or LP as described below. Following treatment, the macrophages were incubated for three days with a concentration of from 100 to 400 units interferon gamma (Amgen Biologicals, Thousand Oaks, Calif.), in medium with 15% pooled normal human serum, at which time the $H_2O_2$ concentration in the cells was determined.

$H_2O_2$ production by macrophages was determined by fluorometric assay using the fluorophore scopoletin (de la Harpe et al., *J. Immunol. Methods* 78: 323 (1985)). Wells containing macrophages were washed and incubated for 90 minutes with a buffered solution of scopoletin (Sigma, St. Louis, Mo.), PMA (Sigma, St. Louis, Mo.), and horseradish peroxidase (HRPO) (Sigma, St. Louis, Mo.). Triggered by PMA, an activated macrophage releases $H_2O_2$ which oxidizes scopoletin to a non-fluorescent product in a reaction catalyzed by HRPO. The amount of $H_2O_2$ released per culture is determined as nanomoles $H_2O_2$. To control for variations in cell numbers from culture to culture, the data were normalized to µg of DNA per culture; all data are presented as nanomoles $H_2O_2$ released/µg DNA/hour. DNA was determined by a fluorescence assay (Kissane et al., *J. Biol. Chem.* 233: 189 (1958).

B. CGRP Inhibition of Macrophage Function

Figure 5:
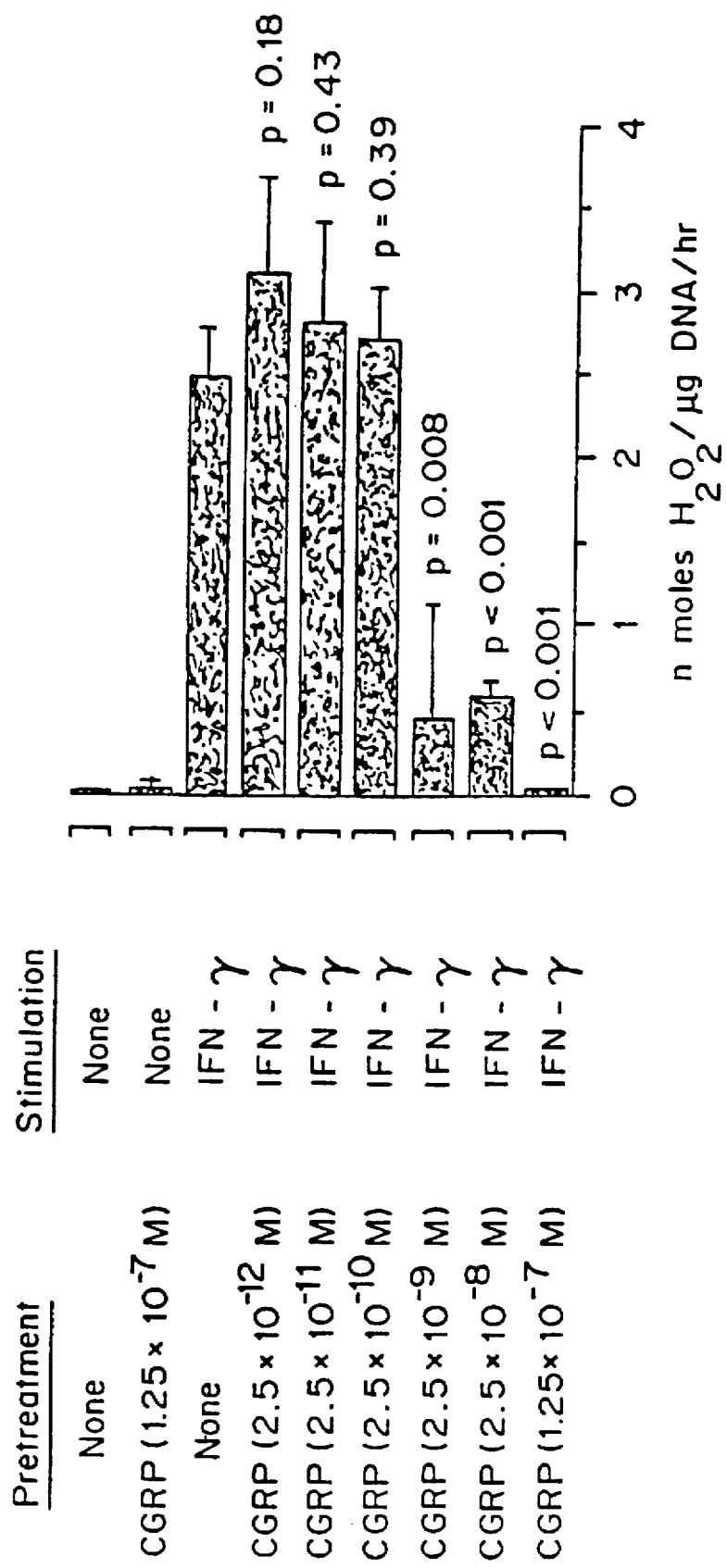
FIG. 5 is a bar graph showing the effect of CGRP on $H_2O_2$ production of human macrophages pretreated with Interferon-γ; the bars represent mean $H_2O_2$ production for triplicate cultures±standard deviation (SD)

Human macrophage monolayers were pretreated for three hours with varying concentrations of human CGRP. The cells were activated with IFN-γ (100 to 400 units/per ml.) for 72 hrs. The amount Of $H_2O_2$ produced by the cells was then determined according to the above procedure. The bars in FIG. 5 represent mean $H_2O_2$ production for triplicate cultures±SD. The p values were derived by comparing the mean $H_2O_2$ response obtained in each of the CGRP-treated groups with the $H_2O_2$ response obtained in the positive control cultures not treated with CGRP but stimulated with IFN-γ. Similar results were obtained in 4 replicate experiments. CGRP was found to markedly inhibit the ability of the macrophages to produce $H_2O_2$ response to IFN-γ (FIG. 5). Concentrations of CGRP as low as $2.5\times10^{-9}$ M significantly inhibited $H_2O_2$ production by the macrophages; higher concentrations completely abrogated the production of $H_2O_2$ (FIG. 5). Results given in FIG. 5 utilize 200 units/ml of IFN-γ, the optimal concentration to stimulate the macrophages. Similar results were obtained using the other test doses. Concentrations of IFN-γ were within 100 units/ml of elicited levels of $H_2O_2$ production by the macrophages which were significantly different than background values.

C. Calcitonin Inhibition of Macrophage Function

Figure 6:
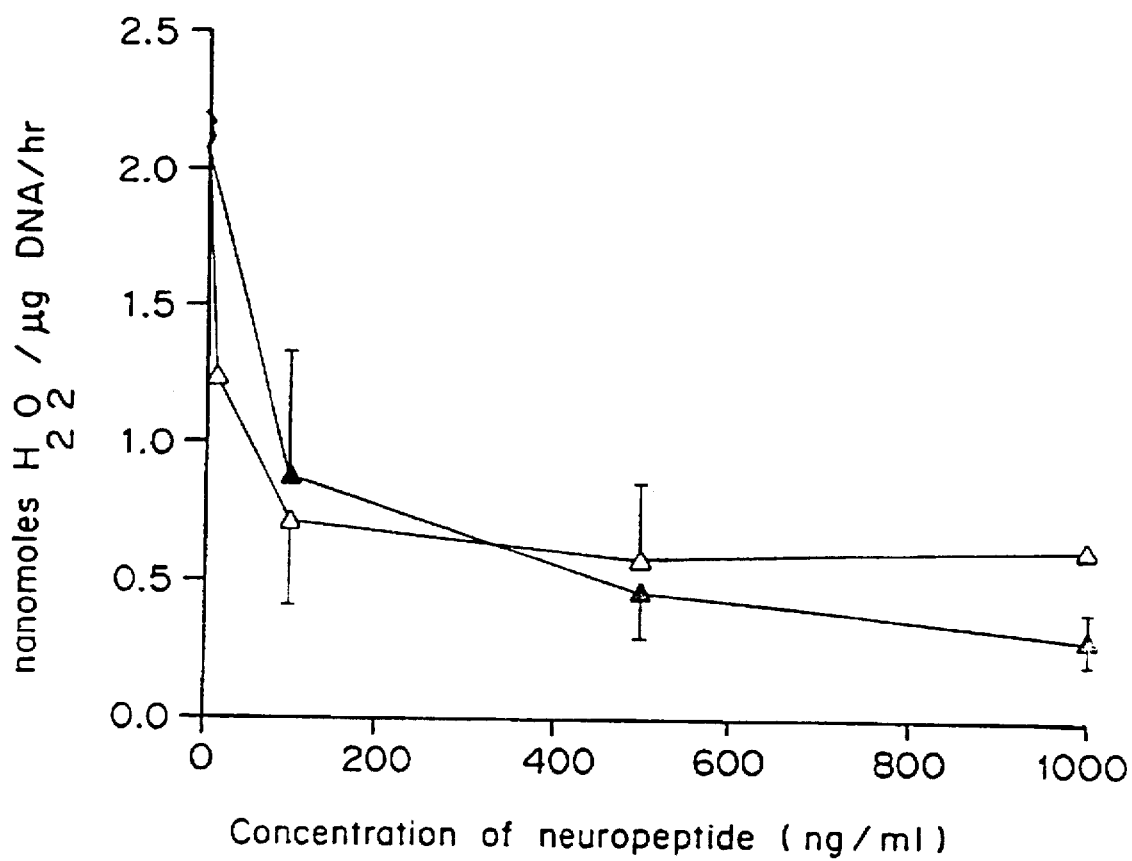
FIG. 6 is a graph comparing the effect of two neuropeptides, calcitonin (Δ) and CGRP ▲ on macrophage function (vertical bars equal standard deviation)
Figure 7:
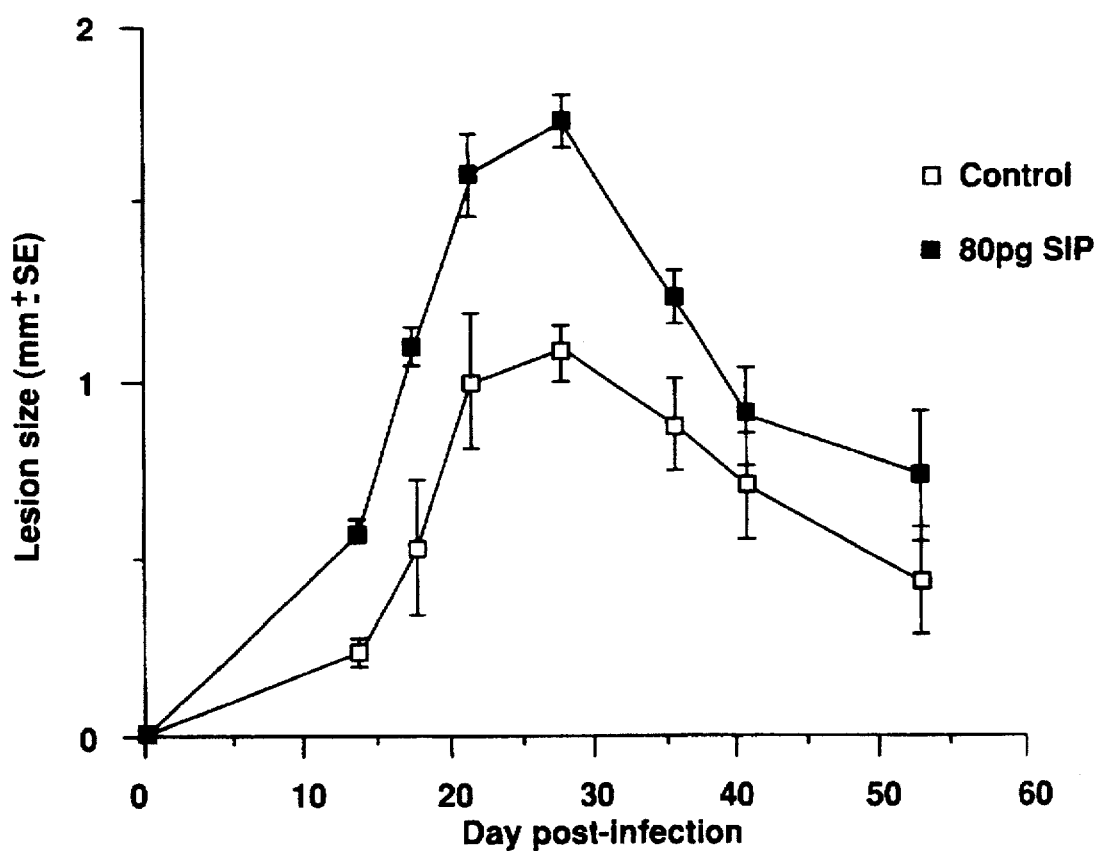
FIG. 7 is a graph showing the effect of recombinant LP protein on Leishmaniasis infection in mice, demonstrated by the size of foot lesions of infected mice mice which were administered recombinant LP protein as compared with control mice.
Figure 8:
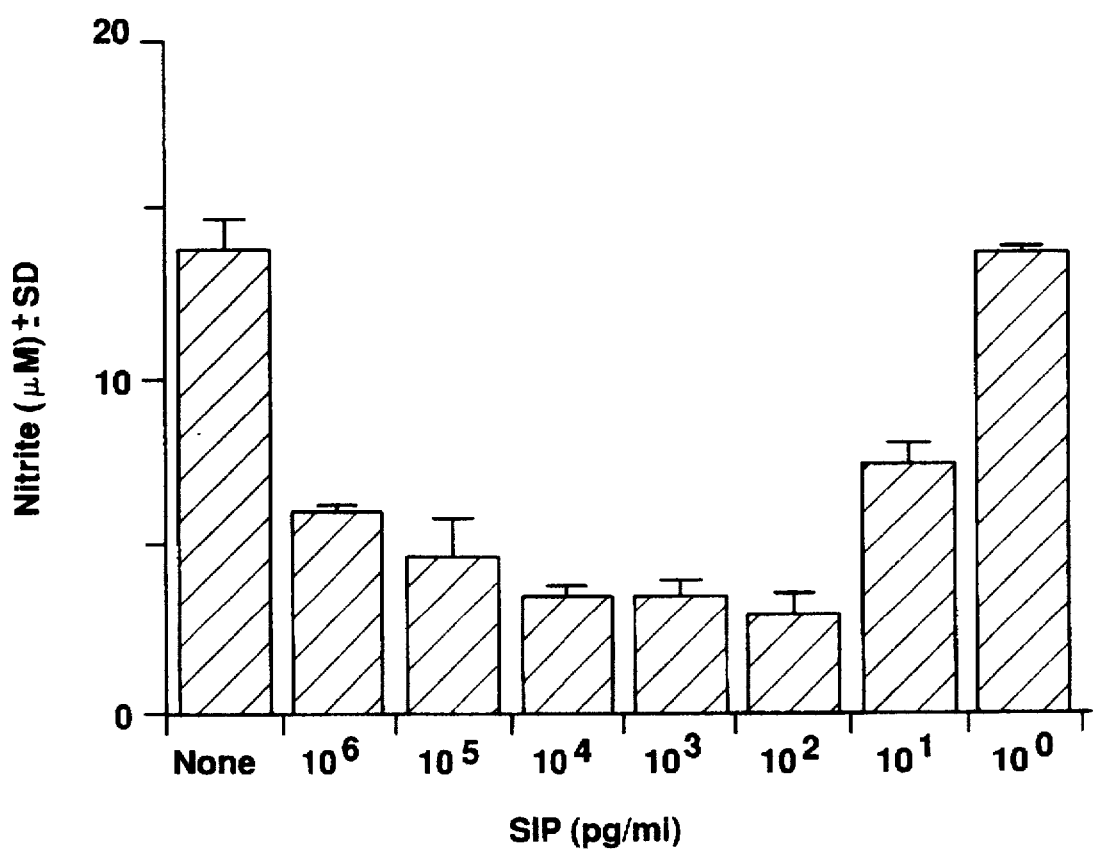
FIG. 8 is a graph showing levels of nitric oxide production by macrophages stimulated with lipopolysaccharide following incubation with increasing amounts of recombinant LP protein.
Figure 9:
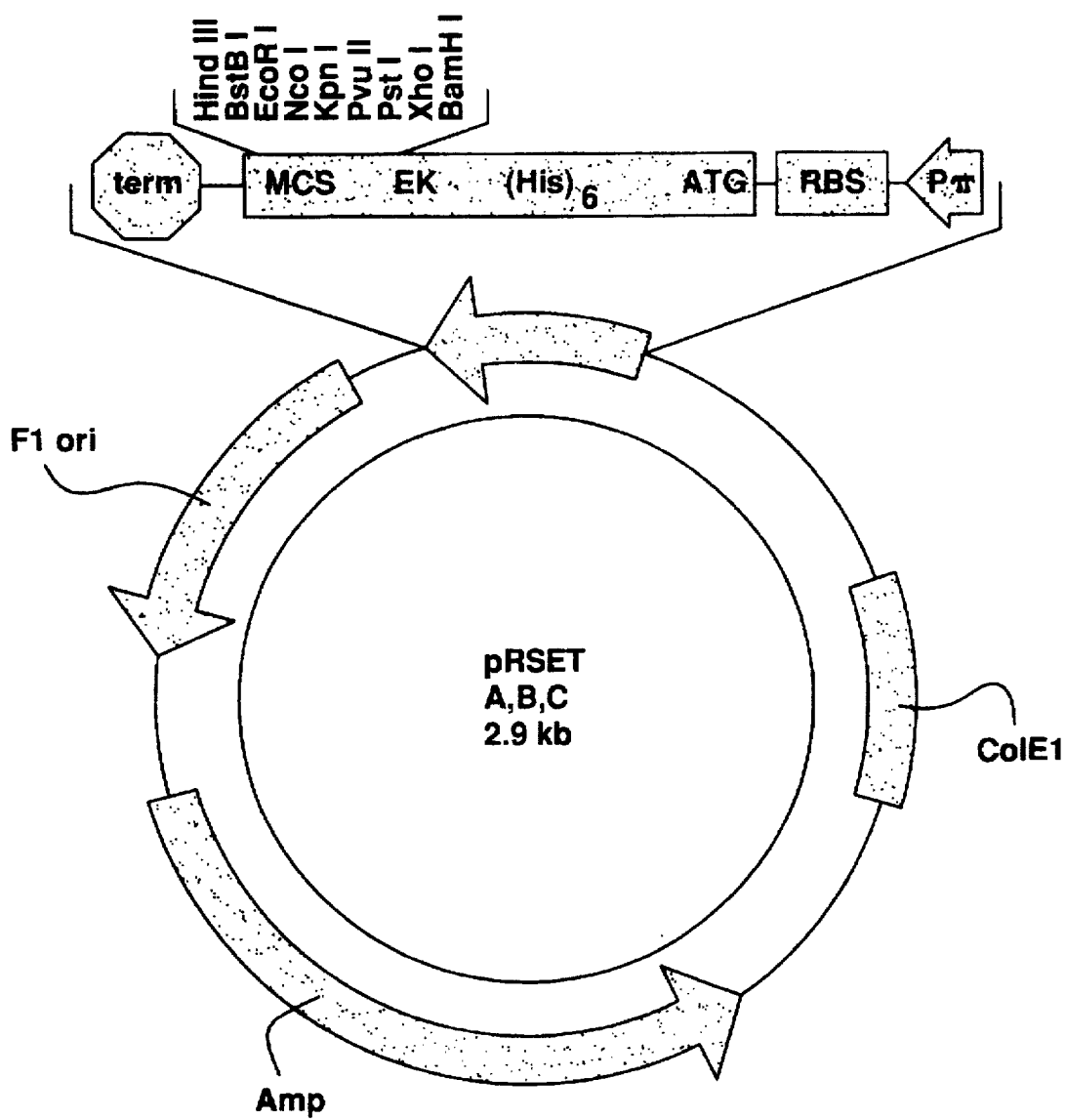
FIG. 9 is a schematic representation of an expression vector, pRSET, used to express a recombinant LP fusion protein.

Human macrophages were treated with the amounts of either CGRP ▲ or calcitonin (Δ) indicated in FIG. 6, as a preincubation step for 3 hrs. The same procedure was followed as described above for CGRP. The cells were rinsed and IFN-γ (200 units/ml) was added. After 3 days incubation, $H_2O_2$ production was determined. The bars represent mean $H_2O_2$ production for triplicate cultures±SD. Since CGRP and calcitonin are nearly identical in molecular weight, 1000 ng/ml, a concentration of $2.5\times10^{-7}$M, was used for the two substances. Calcitonin was found to inhibit $H_2O_2$ production by macrophages to a degree similar to that seen with CGRP (FIG. 6).

D. LP Inhibition of Macrophage Function

Human macrophages were pretreated with varying doses of sand fly salivary gland lysates containing LP or medium for 3 hrs. The salivary material was washed away and the cells were activated with IFN-γ (200 units/ml). Three days later the amount of $H_2O_2$ produced by the cells in response to IFN-γ was determined as pM $H_2O_2$ per culture±SD. These data were normalized to the µg of DNA/culture to control for variation in cell numbers from culture to culture. The inhibition of the IFN-γ induced $H_2O_2$ response of the macrophages is shown in the Table below.

TABLE 4

| Pretreatment | Stimulation | Response {pM $H_2O_2$/ µg DNA} |
|---|---|---|
| None | None | 20 ± 6 |
| Saliva {1 µg/ml} | None | 20 ± 0 |
| None | IFN-γ | 720 ± 190 |
| None | Saliva {1 µg/ml} + IFN-γ | 1170 ± 80* |
| Saliva {1 µg/ml} | IFN-γ | 80 ± 60 |
| None | Saliva {500 ng/ml} + IFN-γ | 960 ± 120* |
| Saliva {500 ng/ml} | IFN-γ | 190 ± 110 |

*No inhibition of the IFN-γ induced response since pretreatment with lysate required for inhibition.

E. CGRP Inhibition of Macrophage Presentation of Antigen

An OVA-specific T-cell line was produced in BALB/c mice (Titus et al., *J. Immunol.* 133:1594 (1984)). The line was L3T4$^+$ and was maintained by successive cycles of restimulation and rest in vitro (Kimono et al., *J. Exp. Med.* 152:759 (1980)). As a source antigen-presenting cells, BALB/c peritoneal cells (Titus et al., *Clin. Exp. Immunol.* 55:157, 1984) were placed into microtiter wells ($10^4$/well) in Dulbecco's modified Eagle's medium (DMEM) (Maryanski et al., *Eur. J Immunol.* 12:401 (1982) supplemented with 5% fetal calf serum (Hyclone, Logan, Utah) and cultured overnight. Non-adherent cells were rinsed out of the wells, and medium with or without rat CGRP ($1.25\times10^{-7}$M) was added as a pre-incubation step. Three hours later the wells were rinsed to remove the CGRP and the indicated number of OVA-specific T-cells (Sigma, St. Louis, Mo.) were added. At varying times thereafter, the wells were pulsed with 1 µCi$^3$H methylthymidine ($^3$H TdR) (Amersham, Arlington Heights, Ill.) and thymidine incorporation was assessed (Titus et al., *J. Immunol.* 133:1594 (1984)).

BALB/c peritoneal macrophages ($10^4$/well) were used as antigen-presenting cells. The macrophages were preincubated in $1.25\times10^{-7}$M rat CGRP for three hrs., and the CGRP was then washed away. OVA-specific T-cells and OVA were then added to the cultures to assist the ability of the CGRP-treated macrophages to present antigen as measured by the degree of proliferation of the T-cells. Forty-eight hours later the cultures were pulsed with $^3$H TdR to assess the degree of proliferation of the T-cells. The numbers in Table 5 below represent the mean thymidine incorporation of quadruplicate cultures±SD. Background responses (macrophages+T-cells but no OVA, or T-cells+OVA but no macrophages) ranged between 300 to 500 CPM. Similar results were obtained with varying numbers ($10^3$ to $2\times10^4$/well) of peritoneal cell macrophages. The results in the Table indicate that the ability of murine macrophages to present OVA to an OVA-specific T-cell line was inhibited by CGRP. Similar results were obtained with different numbers of T-cells and different doses of OVA to stimulate the cultures.

In addition, the inhibition of macrophage antigen presentation by CGRP was not due to simply delaying the kinetics of the response of the OVA-specific T-cells, since similar inhibition of proliferation of the T-cells was observed at day 2 of culture.

TABLE 5

| Macrophages preincubated in | Number of T cells/well | Response (CPM ± SD) 200 mg/ml OVA | to stimulation with 400 mg/ml OVA |
|---|---|---|---|
| Medium | 15,000 | 5,710 ± 1,300 | 8,450 ± 1,140 |
| CGRP | 15,000 | 1,620 ± 910 | 2,620 ± 700 |
| Medium | 30,000 | 5,230 ± 1,150 | 10,970 ± 800 |
| CGRP | 30,000 | 830 ± 500 | 3,380 ± 1,870 |

F. LP Inhibition of Macrophage Presentation of Antigen

The procedure followed was the same as that for CGRP. BALB/c peritoneal macrophages ($2 \times 10^4$/well) were preincubated with medium alone (positive i control) or with the indicated concentrations of *L. longipalpis* salivary gland lysates containing LP for 3 hrs and rinsed free of the material. $2'10^4$ Leishmania specific T cells and $2 \times 10^4$ *L. mania* were then added to the cultures. Twenty-four hrs later the cultures were pulsed with $^3H$ to assess the degree of proliferation of the T cells. The numbers in Table 6 below represent the mean thymidine incorporation of triplicate cultures±SD.

TABLE 6

| Macrophages preincubated in | Response {Mean 3H TdR incorporation} | % inhibition |
|---|---|---|
| Medium | 2065 ± 621 | N/A |
| 1 gland/ml | 726 ± 460 | 65 |
| 0.2 gland/ml | 1002 ± 901 | 51 |
| 0.05 gland/ml | 1882 ± 395 | 9 |

EXAMPLE 7

Expression of a Recombinant Immunosuppressive LP Protein

A. Purification of an LP Protein

A cDNA encoding a *Lutzomyia longipalpis* protein (an "LP Protein") isolated from salivary glands of sand flies from the LaPinha cave region of Brazil was obtained from Alon Warburg and Greg Lanzaro (NIH). This protein was found to have substantially the same amino acid sequence as the protein shown in SEQ ID NO:4. This protein was expressed in *E. coli* as a polyHis fusion protein. Briefly, the cDNA encoding this protein was amplified by polymerase chain reaction (PCR) using opposing synthetic oligonucleotides homologous to the flanking coding DNA and reaction conditions as described by Skelly et al. (1993) *Mol. Biochem. Parasitol.* 60:93–104. The PCR oligonucleotides 5' GGGAATTCGC TAGCTGTGAT GCAACATG 3' (SEQ ID NO:7) and 5' GGGAAGCTTC CTCAATCTTT TACTTTCC 3' (SEQ ID NO:8) contain restriction enzyme recognition sites at their 5' ends to permit asymmetric ligation of the amplified DNA into the *E. coli* expression vector, pRSET, shown in FIG. 9. Following this ligation, the coding DNA becomes fused to the vector encoded polyhistidine domain at the amino-terminal coding end.

The resulting expression plasmid was introduced into *E. coli* and the culture was induced for expression of the fusion protein as recommended by the manufacturer. Inclusion bodies were purified from the induced *E. coli* by the method of Lin et al. (1991) *Biotechniques* 11:748–753 and dissolved into 50 mM Tris-HCl, 5M guanidine hydrochloride, pH 8.0 (buffer D).

A 1 ml chelating HiTrap column (Pharmacia, Inc.) was pre-charged with 1 ml of 0.1M nickel sulfate, washed with water and then buffer D, then loaded with the soluble inclusion body protein. After washing with buffer D until no more protein was eluting the column buffer was changed to 50 mM phosphate buffer, 0.5M NaCl, pH 7.5 (Start buffer). Bound protein was eluted by washing the column with 3 ml of 50 mM phosphate buffer, 0.5M NaCl, 0.5M EDTA, pH 7.5 (Chelating buffer), then collecting the next 1 ml over a 50 min period using a 0.02 ml/min flow rate on an FPLC (Pharmacia, Inc.). The eluates from several preparations were pooled and centrifuged in a microfuge and the fusion protein obtained and washed twice with PBS prior to use in the following assays.

B. Immunosuppressive Activity of the Recombinant LP Protein as Demonstrated by Exacerbation of Cutaneous Leishmaniasis In order to assay for immunosuppressive activity, the recombinant LP protein described in subsection A above was tested for the ability to exacerbate infection of mice with *Leishmania major* substantially as described in Titus et al. (1988) *Science* 239, 1306 and Theodos et al. (1991) *Infect. Immun.* 59, 1592–1598.

Briefly, groups of 4 CBA mice each were injected subcutaneously in the footpad with $10^5$ *L. major* promastigotes alone or $10^5$ parasites admixed with 80 pg of LP protein. Lesion development was followed by measuring the increase in thickness of the injected footpad compared to the thickness of the contralateral uninjected control footpad. The results are shown in FIG. 7.

FIG. 7 demonstrates that the recombinant LP protein greatly exacerbated Leishmania infection in mice as measured by a substantial increase in the size of lesions present on the footpads of infected mice. Therefore, it appears that the LP protein is responsible for the immunosuppressive qualities of sand fly saliva.

C. Immunosuppressive Activity of the Recombinant LP Protein as Demonstrated by Inhibition of Nitric Oxide Production by Macrophages In order to assay for immunosuppressive activity, the recombinant LP protein described in subsection A above was tested for its ability to inhibit nitric oxide (NO) production by macrophages as follows:

Macrophage cells from the RAW 264.7 cell line (Drapier et al. (1988) *J. Immunol.* 140:2829) were preincubated with various concentrations of LP protein as indicated in FIG. 8. The cells were then stimulated with 1 μg/ml lipopolysaccharide protein (LPS) and NO production was monitored 2 hours later by measuring nitrite in the supernatants of the cultures. Nitrite was measured by the method described in Ding et al. (1988) *J. Immunol.* 141:2407. Briefly, levels of nitrite in the supernatants of the cultures were assessed by the Greiss reaction as follows. 50 μl cell culture supernatants were mixed with 50 μl of Greiss reagent [1% sulfanilamide, 0.1% N-(1-naphthyl)ethyl-enediamine dihydrochloride in 2.5% phosphoric acid] and incubated at room temperature for 10 minutes. Absorbance was measured at 570 nm. Concentration of $NO_2$ in the supernatant was determined by comparison to a standard curve generated with dilutions of $NaNO_2$. The results are shown in FIG. 8.

FIG. 8 demonstrates the potency of the immunosuppressive effect of the recombinant LP protein at optimum concentrations ranging from $10^6$ to $10^1$ pg/ml, as measured by a significant decrease in NO production by macrophages preincubated with the LP protein.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references and published patent applications cited throughout this application are hereby incorporated by reference.

What is claimed is:

1. An isolated nucleic acid comprising a nucleotide sequence encoding a fragment of the amino acid sequence shown in SEQ ID NO:2, wherein the fragment comprises 10 or more amino acid residues.

2. A recombinant expression vector comprising the nucleic acid of claim 1.

3. A host cell transformed with the recombinant expression vector of claim 2.

4. An isolated nucleic acid comprising a nucleotide sequence encoding a fragment of the amino acid sequence shown in SEQ ID NO:4, wherein the fragment comprises 10 or more amino acid residues.

5. A recombinant expression vector comprising the nucleic acid of claim 4.

6. A host cell transformed with the recombinant expression vector of claim 5.

7. An isolated nucleic acid of either of claims 1 or 4 encoding a peptide having between 10–20 amino acid residues.

8. An isolated nucleic acid of either of claims 1 or 4 encoding a peptide having 20 or more amino acid residues.

9. An isolated nucleic acid of either of claims 1 or 4 encoding a peptide having vasodilatory or immunosuppressive activity.

10. An isolated nucleic acid comprising the coding region of the nucleotide sequence shown in SEQ ID NO:3.

11. An isolated nucleic acid of claim 10 wherein the coding region comprises nucleotides 52 through 240 of SEQ ID NO:3.

12. A recombinant expression vector comprising the nucleic acid of claim 11.

13. A host cell transformed with the recombinant expression vector of claim 12.

14. An isolated nucleic acid comprising a nucleotide sequence encoding a mature peptide comprising an amino acid sequence shown in SEQ ID NO:4.

15. A recombinant expression vector comprising the nucleic acid of claim 14.

16. A host cell transformed with the recombinant expression vector of claim 15.

17. An isolated nucleic acid of claim 14 wherein the mature peptide comprises amino acid residues 18 through 80 of SEQ ID NO:4.

18. A recombinant expression vector comprising the nucleic acid of claim 17.

19. A host cell transformed with the recombinant expression vector of claim 18.

20. An isolated nucleic acid comprising the nucleotide sequence shown in SEQ ID NO:1.

21. A recombinant expression vector comprising the nucleic acid of claim 20.

22. A host cell transformed with the recombinant expression vector of claim 21.

23. An isolated nucleic acid comprising the nucleotide sequence shown in SEQ ID NO:3.

24. A recombinant expression vector comprising the nucleic acid of claim 23.

25. A host cell transformed with the recombinant expression vector of claim 24.

* * * * *

UNITED STATES PATENT AND TRADEMARK OFFICE
CERTIFICATE OF CORRECTION

PATENT NO. : 5,763,271
DATED : June 9, 1998
INVENTOR(S) : Ribeiro et al.

It is certified that error appears in the above-identified patent and that said Letters Patent is hereby corrected as shown below:

On the title page:

[63] This application is a continuation of U.S. Serial No. 08/137,691, filed on October 15, 1993, Patent No. 5,397,772, which is a continuation of U.S. Serial No. 07/778,159, filed on December 26, 1991, abandoned, which is a continuation of PCT/US90/03746, filed on June 29, 1990, which is a continuation of U.S. Serial No. 07/374,080, filed on June 29, 1989, abandoned.

Signed and Sealed this

Tenth Day of November 1998

*Attest:*

BRUCE LEHMAN

*Attesting Officer*  *Commissioner of Patents and Trademarks*